United States Patent
Hinrichs et al.

(10) Patent No.: US 10,391,047 B2
(45) Date of Patent: Aug. 27, 2019

(54) MOUTHRINSE FORMULATIONS COMPRISING FLUORIDE AND A METAL SALT OF PYRROLIDONE CARBOXYLIC ACID

(71) Applicant: GABA International Holding GmbH, Therwil (CH)

(72) Inventors: Ruth Hinrichs, Therwil (CH); Stephanie Jakumeit, Grenzach-Wyhlen (DE); Turan Matur, Binningen (CH)

(73) Assignee: Colgate-Palmolive Company, New York, NY (US)

( * ) Notice: Subject to any disclaimer, the term of this patent is extended or adjusted under 35 U.S.C. 154(b) by 59 days.

(21) Appl. No.: 15/532,395

(22) PCT Filed: Dec. 18, 2014

(86) PCT No.: PCT/EP2014/078595
§ 371 (c)(1),
(2) Date: Jun. 1, 2017

(87) PCT Pub. No.: WO2016/096028
PCT Pub. Date: Jun. 23, 2016

(65) Prior Publication Data
US 2017/0348216 A1 Dec. 7, 2017

(51) Int. Cl.
| | | |
|---|---|---|
| A61K 8/21 | (2006.01) | |
| A61K 8/49 | (2006.01) | |
| A61K 8/18 | (2006.01) | |
| A61K 8/365 | (2006.01) | |
| A61Q 11/00 | (2006.01) | |

(52) U.S. Cl.
CPC .............. *A61K 8/4913* (2013.01); *A61K 8/18* (2013.01); *A61K 8/21* (2013.01); *A61K 8/365* (2013.01); *A61Q 11/00* (2013.01)

(58) Field of Classification Search
CPC .................................. A61K 8/21; A61K 8/19
See application file for complete search history.

(56) References Cited

U.S. PATENT DOCUMENTS

| | | | |
|---|---|---|---|
| 4,568,540 A * | 2/1986 | Asano | A61K 8/21 424/52 |
| 2005/0025720 A1 | 2/2005 | Bailey | |
| 2010/0158820 A1 | 6/2010 | Bailey | |
| 2012/0034280 A1 | 2/2012 | Cohen et al. | |
| 2013/0209375 A1 | 8/2013 | Moya Argilagos et al. | |

FOREIGN PATENT DOCUMENTS

| | | |
|---|---|---|
| EP | 0162574 | 11/1985 |
| EP | 1227789 | 9/2004 |
| EP | 1555995 | 12/2011 |
| EP | 2404502 | 1/2012 |
| WO | WO 2009/130319 | 10/2009 |

OTHER PUBLICATIONS

Coswell, 2010, "Repair & Protect Toothpaste." Mintel Database GNPD AN 1426203.
International Search Report and Written Opinion of the International Searching Authority in International Application No. PCT/EP2014/078595, dated Jul. 14, 2015.

* cited by examiner

*Primary Examiner* — Benjamin J Packard

(57) ABSTRACT

The present invention provides an oral care composition comprising: (a) a metal salt of pyrrolidone carboxylic acid; (b) at least one fluoride ion source; and (c) at least one a-hydroxy acid or salt thereof; wherein the composition is a mouthwash or a mouthrinse.

25 Claims, No Drawings

MOUTHRINSE FORMULATIONS COMPRISING FLUORIDE AND A METAL SALT OF PYRROLIDONE CARBOXYLIC ACID

BACKGROUND

Bacteria are believed to be a main cause of gingival inflammation. Therefore, antibacterial efficacy of an oral care composition is recognized as being a prerequisite for its utility in treatment of and protection against gingival inflammation. Various metal salts of pyrrolidone carboxylic acid (for example, the zinc salt) have been found to have antibacterial efficacy. However, formulation of stable oral care compositions which contain such salts of pyrrolidone carboxylic acid in combination with certain oral care active ingredients (such as fluorides) has been found to be problematic.

BRIEF SUMMARY

In a first aspect, the present invention provides an oral care composition comprising: (a) a metal salt of pyrrolidone carboxylic acid; (b) at least one fluoride ion source; and (c) at least one α-hydroxy acid or salt thereof; wherein the composition is a mouthwash or a mouthrinse.

Optionally, the metal salt of pyrrolidone carboxylic acid is a metal salt of L-pyrrolidone carboxylic acid.

Optionally, the metal salt of pyrrolidone carboxylic acid is zinc pyrrolidone carboxylate, copper pyrrolidone carboxylate, magnesium pyrrolidone carboxylate, or manganese pyrrolidone carboxylate. Further optionally, the metal salt of pyrrolidone carboxylic acid is zinc pyrrolidone carboxylate.

Optionally, the concentration of the metal salt of pyrrolidone carboxylic acid is from 0.05 to 0.5 weight %, optionally from 0.1 to 0.2 weight %, based on the total weight of the composition.

Optionally, the concentration of fluoride ions in the oral care composition is from 0.005 to 0.1 weight %, optionally from 0.009 to 0.06 weight %, based on the total weight of the composition.

Optionally, the total concentration of the at least one fluoride ion source in the composition is from 0.02 to 1.5 weight %, optionally from 0.05 to 0.5 weight %, based on the total weight of the composition.

Optionally, the at least one fluoride ion source comprises stannous fluoride. Further optionally, the concentration of stannous fluoride is from 0.01 to 0.2 weight %, optionally 0.025 to 0.075 weight %, based on the total weight of the composition.

Optionally, the at least one fluoride ion source is a combination of stannous fluoride and sodium fluoride. Further optionally, the concentration of stannous fluoride is from 0.025 to 0.075 weight % and the concentration of sodium fluoride is from 0.015 to 0.075 weight %, based on the total weight of the composition. Optionally, the weight ratio of stannous fluoride to sodium fluoride is from 2:1 to 1:1, optionally about 1.85:1

Optionally, the at least one fluoride ion source is a combination of stannous fluoride and amine fluoride. Further optionally, the concentration of stannous fluoride is from 0.025 to 0.075 weight % and the concentration of amine fluoride is from 0.05 to 0.5 weight %, based on the total weight of the composition. Optionally, the weight ratio of amine fluoride to stannous fluoride is from 6:1 to 1:1, optionally about 3.15:1.

Optionally, the salt of the at least one α-hydroxy acid is the sodium salt.

Optionally, the at least one α-hydroxy acid is a $C_3$ to $C_7$ α-hydroxy acid, optionally a $C_4$ to $C_6$ α-hydroxy acid. Further optionally, the at least one α-hydroxy acid is malic acid, tartaric acid, α-hydroxy glutaric acid, gluconic acid, or a salt thereof. Optionally, the at least one α-hydroxy acid or salt thereof is selected from malic acid and sodium-D-gluconate.

Optionally, the at least one α-hydroxy acid or salt thereof is malic acid. Further optionally, the concentration of malic acid is from 0.05 to 0.5 weight %, optionally from 0.1 to 0.2 weight %, based on the total weight of the composition.

Optionally, the at least one α-hydroxy acid or salt thereof is sodium-D-gluconate. Further optionally, the concentration of sodium-D-gluconate is from 0.05 to 0.5 weight %, optionally from 0.2 to 0.4 weight %, based on the total weight of the composition.

In a second aspect, the present invention provides a method of preventing turbidity in an oral care composition comprising a metal salt of pyrrolidone carboxylic acid and at least one fluoride ion source, wherein the method comprises formulating the oral care composition to comprise at least one α-hydroxy acid or salt thereof, and wherein the composition is a mouthwash or a mouthrinse.

Optionally, the metal salt of pyrrolidone carboxylic acid is a metal salt of L-pyrrolidone carboxylic acid.

Optionally, the metal salt of pyrrolidone carboxylic acid is zinc pyrrolidone carboxylate, copper pyrrolidone carboxylate, magnesium pyrrolidone carboxylate, or manganese pyrrolidone carboxylate. Further optionally the metal salt of pyrrolidone carboxylic acid is zinc pyrrolidone carboxylate.

Optionally, the concentration of the metal salt of pyrrolidone carboxylic acid in the oral care composition is from 0.05 to 0.5 weight %, optionally from 0.1 to 0.2 weight %, based on the total weight of the composition.

Optionally, the concentration of fluoride ions in the oral care composition is from 0.005 to 0.1 weight %, optionally from 0.009 to 0.06 weight %, based on the total weight of the composition.

Optionally, the total concentration of the at least one fluoride ion source in the composition is from 0.02 to 1.5 weight %, optionally from 0.05 to 0.5 weight %, based on the total weight of the composition.

Optionally, the at least one fluoride ion source comprises stannous fluoride. Further optionally, the concentration of stannous fluoride in the composition is from 0.01 to 0.2 weight %, optionally 0.025 to 0.075 weight %, based on the total weight of the composition.

Optionally, the at least one fluoride ion source is a combination of stannous fluoride and sodium fluoride. Further optionally, the concentration of stannous fluoride is from 0.025 to 0.075 weight % and the concentration of sodium fluoride is from 0.015 to 0.075 weight %, based on the total weight of the composition. Optionally, the weight ratio of stannous fluoride to sodium fluoride is from 2:1 to 1:1, optionally about 1.85:1

Optionally, the at least one fluoride ion source is a combination of stannous fluoride and amine fluoride. Further optionally, the concentration of stannous fluoride is from 0.025 to 0.075 weight % and the concentration of amine fluoride is from 0.05 to 0.5 weight %, based on the total weight of the composition. Optionally, the weight ratio of amine fluoride to stannous fluoride is from 6:1 to 1:1, optionally about 3.15:1.

Optionally, the salt of the at least one α-hydroxy acid is the sodium salt.

Optionally, the at least one α-hydroxy acid is a $C_3$ to $C_7$ α-hydroxy acid, optionally a $C_4$ to $C_6$ α-hydroxy acid. Further optionally, the at least one α-hydroxy acid is malic acid, tartaric acid, α-hydroxy glutaric acid, gluconic acid, or a salt thereof. Still further optionally, the salt is a sodium salt.

Optionally, the at least one α-hydroxy acid or salt thereof is selected from malic acid and sodium-D-gluconate.

Optionally, the at least one α-hydroxy acid or salt thereof is malic acid. Further optionally, the concentration of malic acid is from 0.05 to 0.5 weight %, optionally from 0.1 to 0.2 weight %, based on the total weight of the composition.

Optionally, the at least one α-hydroxy acid or salt thereof is sodium-D-gluconate. Further optionally, the concentration of sodium-D-gluconate is from 0.05 to 0.5 weight %, optionally from 0.2 to 0.4 weight %, based on the total weight of the composition.

In a third aspect, the present invention provides the use of an α-hydroxy acid or salt thereof to prevent turbidity in an oral care composition comprising a metal salt of pyrrolidone carboxylic acid and at least one fluoride ion source, wherein the composition is a mouthwash or a mouthrinse.

In a fourth aspect, the present invention provides a method of reducing staining of teeth by an oral care composition comprising a metal salt of pyrrolidone carboxylic acid and a stannous ion source, wherein the method comprises formulating the oral care composition to comprise a gluconate salt, and wherein the composition is a mouthwash or a mouthrinse.

Optionally, the metal salt of pyrrolidone carboxylic acid is a metal salt of L-pyrrolidone carboxylic acid.

Optionally, the metal salt of pyrrolidone carboxylic acid is zinc pyrrolidone carboxylate, copper pyrrolidone carboxylate, magnesium pyrrolidone carboxylate, or manganese pyrrolidone carboxylate. Further optionally, the metal salt of pyrrolidone carboxylic acid is zinc pyrrolidone carboxylate.

Optionally, the concentration of the metal salt of pyrrolidone carboxylic acid in the oral care composition is from 0.05 to 0.5 weight %, optionally from 0.1 to 0.2 weight %, based on the total weight of the composition.

Optionally, the stannous ion source is stannous fluoride. Further optionally, the concentration of stannous fluoride in the composition is from 0.01 to 0.2 weight %, optionally 0.025 to 0.075 weight %, based on the total weight of the composition.

Optionally, the composition further comprises sodium fluoride. Further optionally the concentration of stannous fluoride is from 0.025 to 0.075 weight % and the concentration of sodium fluoride is from 0.015 to 0.075 weight %, based on the total weight of the composition. Further optionally, the weight ratio of stannous fluoride to sodium fluoride is from 2:1 to 1:1, optionally about 1.85:1

Optionally, the composition further comprises amine fluoride. Further optionally the concentration of stannous fluoride is from 0.025 to 0.075 weight % and the concentration of amine fluoride is from 0.05 to 0.5 weight %, based on the total weight of the composition. Further optionally, the weight ratio of amine fluoride to stannous fluoride is from 6:1 to 1:1, optionally about 3.15:1.

Optionally, the composition comprises fluoride ions in a concentration of from 0.005 to 0.1 weight %, optionally from 0.009 to 0.06 weight %, based on the total weight of the composition.

Optionally, the gluconate salt is sodium-D-gluconate. Further optionally the concentration of sodium-D-gluconate in the composition is from 0.05 to 0.5 weight %, yet further optionally from 0.2 to 0.4 weight %, based on the total weight of the composition.

In a fifth aspect, the present invention provides use of a gluconate salt to reduce staining of teeth by an oral care composition comprising a metal salt of pyrrolidone carboxylic acid and a stannous ion source, wherein the composition is a mouthwash or a mouthrinse.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

All ratios as expressed herein should be understood to refer to ratios by weight, unless otherwise specified.

Unless otherwise specified, all experiments as described herein were carried out at 25° C. and under atmospheric pressure.

The present inventors have surprisingly found that, in mouthwash or mouthrinse compositions which contain at least one fluoride ion source and a metal salt of pyrrolidone carboxylic acid, the further inclusion of at least one α-hydroxy acid or salt thereof prevents the compositions from developing a turbid appearance upon aging.

The present invention therefore provides an oral care composition comprising: (a) a metal salt of pyrrolidone carboxylic acid; (b) at least one fluoride ion source; and (c) at least one α-hydroxy acid or salt thereof; wherein the composition is a mouthwash or a mouthrinse.

Pyrrolidone carboxylic acid (also known as PCA; 2-pyrrolidone-5-carboxylic acid; 5-oxoproline; pidolic acid; or pyroglutamic acid) has the structure as shown below:

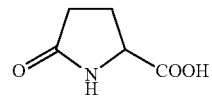

Pyrrolidone carboxylic acid exists as two enantiomers: the L-enantiomer and the D-enantiomer. In certain embodiments of the present invention, the metal salt of pyrrolidone carboxylic acid is a metal salt of L-pyrrolidone carboxylic acid.

In some embodiments, the metal salt of pyrrolidone carboxylic acid is zinc pyrrolidone carboxylate, copper pyrrolidone carboxylate, magnesium pyrrolidone carboxylate, or manganese pyrrolidone carboxylate. In certain embodiments, the metal salt of pyrrolidone carboxylic acid is zinc pyrrolidone carboxylate, for example zinc L-pyrrolidone carboxylate.

In some embodiments, the concentration of the metal salt of pyrrolidone carboxylic acid is from 0.01 to 0.75 weight %, from 0.05 to 0.5 weight %, from 0.075 to 0.4 weight %, from 0.09 to 0.3 weight %, or from 0.1 to 0.2 weight %, based on the total weight of the composition.

In some embodiments, the concentration of fluoride ions in the oral care composition is from 0.005 to 0.1 weight %, from 0.006 to 0.1 weight %, from 0.0075 to 0.075 weight %, from 0.009 to 0.06 weight %, or from 0.02 to 0.03 weight %, or about 0.026 weight % based on the total weight of the composition.

In some embodiments, the total concentration of the at least one fluoride ion source in the composition is from 0.02 to 1.5 weight %, from 0.02 to 1 weight %, from 0.03 to 0.75 weight %, from 0.04 to 0.6 weight %, from 0.05 to 0.5 weight %, or from 0.07 to 0.3 weight %, based on the total weight of the composition.

In some embodiments, the at least one fluoride ion source comprises stannous fluoride. In certain embodiments, the concentration of stannous fluoride is from 0.01 to 0.5 weight %, from 0.01 to 0.2 weight %, from 0.02 to 0.1 weight %, from 0.025 to 0.075 weight %, or from 0.05 to 0.06 weight %, based on the total weight of the composition.

In certain embodiments, the at least one fluoride ion source is a combination of stannous fluoride and sodium fluoride. In certain embodiments, the total concentration of stannous fluoride and sodium fluoride in the composition is from 0.02 to 0.5 weight %, from 0.03 to 0.3 weight %, from 0.05 to 0.2 weight %, or from 0.075 to 0.1 weight %, based on the total weight of the composition. In certain embodiments, the weight ratio of stannous fluoride to sodium fluoride is from 2.5:1 to 1:1.5, from 2:1 to 1:1, from 2:1 to 1.5:1, or about 1.85:1. In some embodiments, the oral care composition comprises from 0.02 to 0.1 weight % stannous fluoride and from 0.01 to 0.1 weight % sodium fluoride, based on the total weight of the composition. In some embodiments, the oral care composition comprises from 0.025 to 0.075 weight % stannous fluoride and from 0.015 to 0.075 weight % sodium fluoride, based on the total weight of the composition. In some embodiments, the oral care composition comprises from 0.05 to 0.06 weight % stannous fluoride and from 0.02 to 0.04 weight % sodium fluoride, based on the total weight of the composition.

In some embodiments, the at least one fluoride ion source is a combination of stannous fluoride and amine fluoride. As used herein, the term "amine fluoride" is used to denote the compound N,N,N'-tris(2-hydroxyethyl)-N'-octadecyl-1,3-diaminopropane dihydrofluoride (also known as "Olaflur", and sometimes written as N,N,N'-tris(2-hydroxyethyl)-N'-octadecyl propane-1,3-diamine dihydrofluoride). In certain embodiments, the total concentration of stannous fluoride and amine fluoride in the composition is from 0.05 to 1 weight %, from 0.05 to 0.5 weight %, from 0.1 to 0.4 weight %, or from 0.2 to 0.3 weight %, based on the total weight of the composition. In certain embodiments, the weight ratio of amine fluoride to stannous fluoride is from 6:1 to 1:1, from 5:1 to 2:1, from 4:1 to 3:1, or about 3.15:1. In some embodiments, the oral care composition comprises from 0.02 to 0.1 weight % stannous fluoride and from 0.05 to 0.9 weight % amine fluoride, based on the total weight of the composition. In some embodiments, the oral care composition comprises from 0.025 to 0.075 weight % stannous fluoride and from 0.05 to 0.5 weight % amine fluoride, based on the total weight of the composition. In some embodiments, the oral care composition comprises from 0.05 to 0.06 weight % stannous fluoride and from 0.1 to 0.2 weight % amine fluoride, based on the total weight of the composition.

In some embodiments, the salt of the at least one α-hydroxy acid is the sodium salt or the potassium salt. In some embodiments, the salt is the sodium salt.

In some embodiments, the at least one α-hydroxy acid is a $C_3$ to $C_7$ α-hydroxy acid, or a $C_4$ to $C_6$ α-hydroxy acid. In certain embodiments, the at least one α-hydroxy acid is malic acid, tartaric acid, α-hydroxy glutaric acid, gluconic acid, or a salt thereof. In certain embodiments, the at least one α-hydroxy acid or salt thereof is selected from malic acid and sodium-D-gluconate.

In some embodiments, the at least one α-hydroxy acid or salt thereof is malic acid. In certain embodiments, the malic acid is a racemic mixture of L-malic acid and D-malic acid. In some embodiments, the concentration of malic acid is from 0.01 to 0.75 weight %, from 0.05 to 0.5 weight %, from 0.075 weight % to 0.3 weight %, or from 0.1 to 0.2 weight %, based on the total weight of the composition.

In some embodiments, the at least one α-hydroxy acid or salt thereof is sodium-D-gluconate. In some embodiments, the concentration of sodium-D-gluconate is from 0.01 to 0.75 weight %, from 0.05 to 0.5 weight %, from 0.1 to 0.5 weight %, or from 0.2 to 0.4 weight %, based on the total weight of the composition.

In a second aspect, the present invention provides a method of preventing turbidity in an oral care composition comprising a metal salt of pyrrolidone carboxylic acid and at least one fluoride ion source, wherein the method comprises formulating the oral care composition to comprise at least one α-hydroxy acid or salt thereof, and wherein the composition is a mouthwash or a mouthrinse. The present invention also provides the use of an α-hydroxy acid or salt thereof to prevent turbidity in an oral care composition comprising a metal salt of pyrrolidone carboxylic acid and at least one fluoride ion source, wherein the composition is a mouthwash or a mouthrinse.

The present inventors have also found that the compositions of the present invention do not stain teeth any more than equivalent formulas which contain a fluoride source but which contain no metal salts of pyrrolidone carboxylic acid and no α-hydroxy acids or salts thereof. In particular, the present inventors have found that compositions of the present invention which contain sodium-D-gluconate stain teeth to a lesser extent than equivalent compositions which contain stannous fluoride and a metal salt of pyrrolidone carboxylic acid but no sodium-D-gluconate (and also as compared to an equivalent composition which contains stannous fluoride but no metal salts of pyrrolidone carboxylic acid and no sodium-D-gluconate). In a fourth aspect, the present invention therefore provides a method of reducing staining of teeth by an oral care composition comprising a metal salt of pyrrolidone carboxylic acid and a stannous ion source, wherein the method comprises formulating the oral care composition to comprise a gluconate salt, and wherein the composition is a mouthwash or a mouthrinse. In a fifth aspect, the present invention also provides use of a gluconate salt to reduce staining of teeth by an oral care composition comprising a metal salt of pyrrolidone carboxylic acid and a stannous ion source, wherein the composition is a mouthwash or a mouthrinse.

In some embodiments of any of the above methods or uses, the metal salt of pyrrolidone carboxylic acid is a metal salt of L-pyrrolidone carboxylic acid. In some embodiments, the metal salt of pyrrolidone carboxylic acid is zinc pyrrolidone carboxylate, copper pyrrolidone carboxylate, magnesium pyrrolidone carboxylate, or manganese pyrrolidone carboxylate. In certain embodiments, wherein the metal salt of pyrrolidone carboxylic acid is zinc pyrrolidone carboxylate, for example zinc L-pyrrolidone carboxylate.

In some embodiments of any of the above methods or uses, the concentration of the metal salt of pyrrolidone carboxylic acid in the composition is from 0.01 to 0.75 weight %, from 0.05 to 0.5 weight %, from 0.075 to 0.4 weight %, from 0.09 to 0.3 weight %, or from 0.1 to 0.2 weight %, based on the total weight of the composition.

In certain embodiments of any of the above methods or uses, the concentration of fluoride ions in the oral care composition is from 0.005 to 0.1 weight %, from 0.006 to 0.1 weight %, from 0.0075 to 0.075 weight %, from 0.009 to 0.06 weight %, or from 0.02 to 0.03 weight %, or about 0.026 weight %, based on the total weight of the composition.

In some embodiments of any of the above methods or uses, the total concentration of the at least one fluoride ion source in the composition is from 0.02 to 1.5 weight %, from 0.02 to 1 weight %, from 0.03 to 0.75 weight %, from 0.04 to 0.6 weight %, from 0.05 to 0.5 weight %, or from 0.07 to 0.3 weight %, based on the total weight of the composition.

In some embodiments of any of the above methods or uses, the at least one fluoride ion source comprises stannous fluoride (or, in some embodiments, the stannous ion source is stannous fluoride). In certain embodiments, the concentration of stannous fluoride is from 0.01 to 0.5 weight %, from 0.01 to 0.2 weight %, from 0.02 to 0.1 weight %, from 0.025 to 0.075 weight %, or from 0.05 to 0.06 weight %, based on the total weight of the composition.

In certain embodiments of any of the above methods or uses, the at least one fluoride ion source is a combination of stannous fluoride and sodium fluoride (or, in some embodiments, the composition comprises sodium fluoride in addition to stannous fluoride). In certain embodiments, the total concentration of stannous fluoride and sodium fluoride in the composition is from 0.02 to 0.5 weight %, from 0.03 to 0.3 weight %, from 0.05 to 0.2 weight %, or from 0.075 to 0.1 weight %, based on the total weight of the composition. In certain embodiments, the weight ratio of stannous fluoride to sodium fluoride is from 2.5:1 to 1:1.5, from 2:1 to 1:1, from 2:1 to 1.5:1, or about 1.85:1. In some embodiments, the oral care composition comprises from 0.02 to 0.1 weight % stannous fluoride and from 0.01 to 0.1 weight % sodium fluoride, based on the total weight of the composition. In some embodiments, the oral care composition comprises from 0.025 to 0.075 weight % stannous fluoride and from 0.015 to 0.075 weight % sodium fluoride, based on the total weight of the composition. In some embodiments, the oral care composition comprises from 0.05 to 0.06 weight % stannous fluoride and from 0.02 to 0.04 weight % sodium fluoride, based on the total weight of the composition.

In some embodiments of any of the above methods or uses, the at least one fluoride ion source is a combination of stannous fluoride and amine fluoride (or, in some embodiments, the composition comprises amine fluoride in addition to stannous fluoride). In certain embodiments, the total concentration of stannous fluoride and amine fluoride in the composition is from 0.05 to 1 weight %, from 0.05 to 0.5 weight %, from 0.1 to 0.4 weight %, or from 0.2 to 0.3 weight %, based on the total weight of the composition. In certain embodiments, the weight ratio of amine fluoride to stannous fluoride is from 6:1 to 1:1, from 5:1 to 2:1, from 4:1 to 3:1, or about 3.15:1. In some embodiments, the oral care composition comprises from 0.02 to 0.1 weight % stannous fluoride and from 0.05 to 0.9 weight % amine fluoride, based on the total weight of the composition. In some embodiments, the oral care composition comprises from 0.025 to 0.075 weight % stannous fluoride and from 0.05 to 0.5 weight % amine fluoride, based on the total weight of the composition. In some embodiments, the oral care composition comprises from 0.05 to 0.06 weight % stannous fluoride and from 0.1 to 0.2 weight % amine fluoride, based on the total weight of the composition.

In some embodiments, the salt of the at least one α-hydroxy acid is the sodium salt or the potassium salt. In some embodiments, the salt is the sodium salt.

In some embodiments of any of the above methods or uses, the at least one α-hydroxy acid is a $C_3$ to $C_7$ α-hydroxy acid, or a $C_4$ to $C_6$ α-hydroxy acid. In certain embodiments, the at least one α-hydroxy acid is malic acid, tartaric acid, α-hydroxy glutaric acid, gluconic acid, or a salt thereof. In certain embodiments, the at least one α-hydroxy acid or salt thereof is selected from malic acid and sodium-D-gluconate.

In some embodiments of any of the above methods or uses, the at least one α-hydroxy acid or salt thereof is malic acid. In certain embodiments, the malic acid is a racemic mixture of L-malic acid and D-malic acid. In some embodiments, the concentration of malic acid is from 0.01 to 0.75 weight %, from 0.05 to 0.5 weight %, from 0.075 weight % to 0.3 weight %, or from 0.1 to 0.2 weight %, based on the total weight of the composition.

In some embodiments of any of the above methods or uses, the at least one α-hydroxy acid or salt thereof is sodium-D-gluconate (or, in some embodiments, the gluconate salt is sodium-D-gluconate). In some embodiments, the concentration of sodium-D-gluconate is from 0.01 to 0.75 weight %, from 0.05 to 0.5 weight %, from 0.1 to 0.5 weight %, or from 0.2 to 0.4 weight %, based on the total weight of the composition.

In any of the above embodiments of the oral care compositions, methods and uses, the compositions may further comprise additional ingredients. These additional ingredients may include, but are not limited to, diluents, surfactants, sweeteners, flavorants, colorants, preservatives, anticalculus or tartar control agents, polymers (such as carboxymethylcellulose or hydroxyethylcellulose) and mixtures thereof.

The oral care compositions of the invention may also comprise at least one surfactant. Any orally acceptable surfactant, such as nonionic or amphoteric surfactants, can be used. One or more surfactants are optionally present in a total amount of about 0.01 wt. % to about 10 wt. %, for example, from about 0.05 wt. % to about 5 wt. %, or from about 0.1 wt. % to about 2 wt. % by total weight of the composition.

The oral care compositions of the present invention may comprise at least one sweetener (such as, for example, sodium saccharin), useful for example to enhance taste of the composition. One or more sweeteners are optionally present in a total amount depending strongly on the particular sweetener(s) selected, but typically 0.005 wt. % to 5 wt. %, by total weight of the composition, optionally 0.005 wt. % to 0.2 wt. %, further optionally 0.05 wt. % to 0.1 wt. % by total weight of the composition.

The compositions of the present invention may also comprise at least one flavorant, useful for example to enhance taste of the composition. One or more flavorants are optionally present in a total amount of from about 0.01 wt.

% to about 5 wt. %, for example, from about 0.03 wt. % to about 2.5 wt. %, optionally about 0.05 wt. % to about 1.5 wt. %, further optionally about 0.1 wt. % to about 0.3 wt. % by total weight of the composition.

The compositions of the invention may comprise at least one colorant. Colorants herein include pigments, dyes, lakes and agents imparting a particular luster or reflectivity such as pearling agents. Any orally acceptable colorant can be used. One or more colorants are optionally present in a total amount of from about 0.0001 wt. % to about 20 wt. %, for example, from about 0.0001 wt. % to about 10 wt. %, from about 0.0001 wt. % to about 5 wt. %, or from about 0.0001 to 0.001 wt. % by total weight of the composition.

The compositions of the present invention may comprise a saliva stimulating agent useful, for example, in amelioration of dry mouth. One or more saliva stimulating agents are optionally present in saliva stimulating effective total amount.

The compositions of the present invention may include antisensitivity agents. Such agents may be added in effective amounts, e.g., from about 0.1 wt. % to about 5 wt. % by weight based on the total weight of the composition, depending on the agent chosen.

EXAMPLES

Example 1

Various mouthrinse compositions were formulated, having base formulas with the amounts of zinc PCA, stannous fluoride, amine fluoride, sodium fluoride, sodium-D-gluconate and malic acid as denoted in Table 1, below. Each of the base formulas also contained 2.4 weight % polyvinylpyrrolidone (PVP).

TABLE 1

| Base formula | Weight % zinc PCA | Weight % stannous fluoride | Weight % amine fluoride | Weight % sodium fluoride | Weight % sodium-D-gluconate | Weight % malic acid |
|---|---|---|---|---|---|---|
| A | 0.100 | 0.054 | 0.170 | 0.000 | 0.250 | 0.000 |
| B | 0.100 | 0.054 | 0.170 | 0.000 | 0.000 | 0.150 |
| C | 0.100 | 0.054 | 0.170 | 0.000 | 0.000 | 0.170 |
| D | 0.100 | 0.054 | 0.170 | 0.000 | 0.275 | 0.000 |
| E | 0.100 | 0.054 | 0.170 | 0.000 | 0.000 | 0.200 |
| F | 0.100 | 0.054 | 0.170 | 0.000 | 0.000 | 0.120 |
| G | 0.150 | 0.054 | 0.170 | 0.000 | 0.000 | 0.150 |
| H | 0.200 | 0.054 | 0.00 | 0.029 | 0.000 | 0.150 |
| I | 0.150 | 0.054 | 0.170 | 0.000 | 0.375 | 0.000 |
| J | 0.150 | 0.054 | 0.170 | 0.000 | 0.300 | 0.000 |
| K | 0.150 | 0.054 | 0.00 | 0.029 | 0.000 | 0.150 |
| L | 0.150 | 0.054 | 0.170 | 0.000 | 0.000 | 0.170 |
| M | 0.138 | 0.054 | 0.170 | 0.000 | 0.375 | 0.000 |
| N | 0.200 | 0.054 | 0.00 | 0.029 | 0.000 | 0.175 |

Various compositions of the present invention were then formulated, which corresponded to these base formulas with the further inclusion of a humectant which was either: xylitol alone (in a concentration of 0.85 weight %, 2.5 weight % or 5 weight %); a combination of 5 weight % xylitol and 3 weight % glycerin; a combination of 5 weight % xylitol with 0.1 weight % propylene glycol; or a combination of 0.15 weight % propylene glycol with either 0.85 weight %, 2.5 weight % or 5 weight % xylitol, based on the total weight of the composition.

Four comparative formulas were also prepared, which contained neither malic acid nor sodium-D-gluconate. These comparative compositions are shown in Table 2, below:

TABLE 2

| Formula | Weight % zinc PCA | Weight % stannous fluoride | Weight % amine fluoride | Weight % sodium fluoride | Weight % xylitol | Weight % glycerin | Weight % PVP | Weight % Propylene glycol |
|---|---|---|---|---|---|---|---|---|
| Comparative I | 0.000 | 0.054 | 0.170 | 0.000 | 0.850 | 0.000 | 0.300 | 0.000 |
| Comparative II | 0.000 | 0.054 | 0.170 | 0.000 | 5.000 | 3.000 | 2.400 | 0.000 |
| Comparative III | 0.100 | 0.054 | 0.170 | 0.000 | 5.000 | 3.000 | 2.400 | 0.000 |
| Comparative IV | 0.100 | 0.054 | 0.170 | 0.000 | 5.000 | 3.000 | 2.400 | 0.200 |

Each of the compositions of the present invention (and also the four comparative compositions) were evaluated in terms of their color and texture after aging for 3 months at 25° C., 6 months at 25° C., 3 months at 40° C., and 6 months at 40° C. These results are summarized in Table 3, below:

TABLE 3

| | Appearance after 3 months at 25° C. | Appearance after 6 months at 25° C. | Appearance after 3 months at 40° C. | Appearance after 6 months at 40° C. |
|---|---|---|---|---|
| Comp. I | Light blue slightly turbid solution; traces of sediments | Light blue slightly turbid solution; traces of sediments | Light blue slightly turbid solution; some sediments | Light blue solution with green tinge; almost turbid solution with some sediments |
| Comp. II | Light blue clear solution without sediments | Light blue clear solution without sediments | Light blue slightly turbid solution; no sediments | Light blue solution with green tinge; slightly turbid solution with minimal sediments |

TABLE 3-continued

|   | Appearance after 3 months at 25° C. | Appearance after 6 months at 25° C. | Appearance after 3 months at 40° C. | Appearance after 6 months at 40° C. |
|---|---|---|---|---|
| Comp. III | Light blue slightly turbid solution with slight sediments | Slightly turbid solution with sediments | Almost turbid solution with some sediments | Almost turbid solution with some sediments |
| Comp. IV | Turbid solution | — | — | — |
| A to B | Light blue clear solution without sediments | Light blue clear solution without sediments | Light blue clear solution without sediments | Light blue clear solution without sediments; some clouding |
| C to E | Light blue clear solution without sediments | Light blue clear solution without sediments | Light blue clear solution without sediments | Light blue clear solution without sediments |
| F | Light blue clear solution without sediments | Light blue clear solution without sediments | Light blue clear solution without sediments | Light blue clear solution; some clouding |
| G to N | Light blue clear solution without sediments | — | Clear solution without sediments | — |

Comparative I (which contained no zinc PCA) remained as a light blue solution after both 3 months and 6 months at 25° C., and also after 3 months at 40° C. A green tinge was observed after aging for 6 months at 40° C. Comparative I was observed to be a slightly turbid solution with traces of sediments after both 3 months and 6 months aging at 25° C., and to be a slightly turbid solution with some sediments after both 3 months and 6 months aging at 40° C.

Comparative II (which also contained no zinc PCA) remained as a light blue solution after both 3 months and 6 months at 25° C., and also after 3 months at 40° C. A green tinge was observed after aging for 6 months at 40° C. Comparative II was observed to be a clear solution without sediments after both 3 months and 6 months aging at 25° C., and to be a slightly turbid solution without (or with only minimal) sediments after both 3 months and 6 months aging at 40° C.

Comparative III (which contained zinc PCA but no sodium-D-gluconate or malic acid) was a light blue slightly turbid solution with slight sediments after 3 months at 25° C., and was a slightly turbid solution with some sediments after 6 months at 25° C. This composition was seen to be an almost turbid solution with some sediments after both 3 and 6 months at 40° C.

Comparative IV (which contained zinc PCA and propylene glycol, but no sodium-D-gluconate or malic acid), was a turbid solution even after 3 months at 25° C.

All of the compositions of the invention which were formulated from base formulas A to N remained as clear, light blue solutions without sediments after 3 months aging at 25° C. and after 3 months aging at 40° C.

The compositions of the invention which were formulated from base formulas A to F also remained as clear, light blue solutions without sediments after 6 months aging at 25° C. The compositions of the invention which were formulated from base formulas A to F also remained as clear, light blue solutions without sediments after 6 months aging at 25° C., however some clouding was seen in the compositions of the invention which were formulated from base formulas A, B and F after 6 months aging at 40° C.

These results demonstrate that the inclusion of sodium-D-gluconate or malic acid in mouthrinse compositions which contain fluoride and zinc PCA reduces the formation of turbidity in the compositions, irrespective of which humectant(s) are included within the compositions.

Example 2

In vitro tests (In Vitro Staining Model) demonstrated that inclusion of sodium-D-gluconate in compositions of the present invention which contain stannous fluoride (Inventive composition I) results in a decrease in staining of the teeth as compared to an equivalent composition which does not contain sodium-D-gluconate (Comparative composition V) and as compared to an equivalent composition which contains neither sodium-D-gluconate nor zinc PCA (Comparative composition I).

Tooth crowns were sectioned in half and embedded in acrylic resin with the enamel surface of the teeth exposed. The tooth surfaces were pre-treated with 1 weight % phytic acid for 1 minute. The whiteness of the teeth was measured using a spectrometer. The teeth were then immersed in human saliva for 2 minutes; rinsed with distilled water; immersed in the test mouth rinse for 30 seconds; rinsed with distilled water; immersed in black tea for 1 minute; and rinsed with distilled water. This cycle of immersion/rinsing was repeated eight times. The whiteness of the teeth was measured again after completion of the eight cycles, and the change in whiteness, ΔE, of the tooth surfaces (as compared to their whiteness before treatment with the mouthrinse) was determined. A smaller value for ΔE indicates a lower level of staining. The results are shown in Table 4, below:

TABLE 4

| Formula | Weight % zinc PCA | Weight % stannous fluoride | Weight % amine fluoride | Weight % sodium-D-gluconate | Weight % xylitol | Weight % polyvinyl-pyrrolidone | ΔE after 8 cycles |
|---|---|---|---|---|---|---|---|
| Comp. I | 0.00 | 0.054 | 0.170 | 0.000 | 0.850 | 0.300 | 20.43 |
| Comp. V | 0.10 | 0.054 | 0.170 | 0.000 | 0.850 | 0.300 | 19.17 |
| Inv. I | 0.10 | 0.054 | 0.170 | 0.260 | 0.850 | 0.300 | 14.45 |

As can be seen from these results, the inclusion of sodium-D-gluconate in the composition resulted in a reduction in the amount of staining caused by the stannous fluoride-containing mouthrinse.

What is claimed is:

1. An oral care composition comprising:
   (a) a metal salt of pyrrolidone carboxylic acid;
   (b) at least one fluoride ion source; and
   (c) at least one α-hydroxy acid or salt thereof;
   wherein the composition is a mouthwash or a mouthrinse.

2. The oral care composition of claim 1, wherein the metal salt of pyrrolidone carboxylic acid is a metal salt of L-pyrrolidone carboxylic acid.

3. The oral care composition of claim 1, wherein the metal salt of pyrrolidone carboxylic acid is zinc pyrrolidone carboxylate, copper pyrrolidone carboxylate, magnesium pyrrolidone carboxylate, or manganese pyrrolidone carboxylate.

4. The oral care composition of claim 3, wherein the metal salt of pyrrolidone carboxylic acid is zinc pyrrolidone carboxylate.

5. The oral care composition of claim 1, wherein the concentration of the metal salt of pyrrolidone carboxylic acid is from 0.05 to 0.5 weight %, based on the total weight of the composition.

6. The oral care composition of claim 1 wherein the at least one fluoride ion source comprises stannous fluoride.

7. The oral care composition of claim 6, wherein the concentration of stannous fluoride is from 0.01 to 0.2 weight %, based on the total weight of the composition.

8. The oral care composition of claim 1, wherein the at least one fluoride ion source is a combination of stannous fluoride and sodium fluoride.

9. The oral care composition of claim 8, wherein the concentration of stannous fluoride is from 0.025 to 0.075 weight and the concentration of sodium fluoride is from 0.015 to 0.075 weight %, based on the total weight of the composition.

10. The oral care composition of claim 8, wherein the weight ratio of stannous fluoride to sodium fluoride is from 2:1 to 1:1.

11. The oral care composition of claim 1, wherein the at least one fluoride ion source is a combination of stannous fluoride and amine fluoride.

12. The oral care composition of claim 11, wherein the concentration of stannous fluoride is from 0.025 to 0.075 weight % and the concentration of amine fluoride is from 0.05 to 0.5 weight %, based on the total weight of the composition.

13. The oral care composition of claim 11, wherein the weight ratio of amine fluoride to stannous fluoride is from 6:1 to 1:1.

14. The oral care composition of claim 1, wherein the salt of the at least one α-hydroxy acid is the sodium salt.

15. The oral care composition of claim 1, wherein the at least one α-hydroxy acid is a $C_3$ to $C_7$ α-hydroxy.

16. The oral care composition of claim 15, wherein the at least one α-hydroxy acid is malic acid, tartaric acid, α-hydroxy glutaric acid, gluconic acid, or a salt thereof.

17. The oral care composition of claim 16, wherein the at least one α-hydroxy acid or salt thereof is selected from malic acid and sodium-D-gluconate.

18. A method of preventing turbidity in an oral care composition comprising a metal salt of pyrrolidone carboxylic acid and at least one fluoride ion source, wherein the method comprises formulating the oral care composition to comprise at least one α-hydroxy acid or salt thereof, and wherein the composition is a mouthwash or a mouthrinse.

19. The method of claim 18, wherein the metal salt of pyrrolidone carboxylic acid is a metal salt of L-pyrrolidone carboxylic acid.

20. The method of claim 18, wherein the metal salt of pyrrolidone carboxylic acid is zinc pyrrolidone carboxylate, copper pyrrolidone carboxylate, magnesium pyrrolidone carboxylate, or manganese pyrrolidone carboxylate.

21. The method of claim 18, wherein the concentration of the metal salt of pyrrolidone carboxylic acid in the oral care composition is from 0.05 to 0.5 weight %, based on the total weight of the composition.

22. The oral care composition of claim 18, wherein the salt of the at least one α-hydroxy acid is the sodium salt.

23. The method of claim 18, wherein the at least one α-hydroxy acid is a $C_3$ to $C_7$ α-hydroxy acid.

24. The method of claim 23, wherein the at least one α-hydroxy acid is malic acid, tartaric acid, α-hydroxy glutaric acid, gluconic acid, or a salt thereof.

25. A method of reducing staining of teeth by an oral care composition comprising a metal salt of pyrrolidone carboxylic acid and a stannous ion source, wherein the method comprises formulating the oral care composition to comprise a gluconate salt, and wherein the composition is a mouthwash or a mouthrinse.

* * * * *

UNITED STATES PATENT AND TRADEMARK OFFICE
CERTIFICATE OF CORRECTION

PATENT NO. : 10,391,047 B2
APPLICATION NO. : 15/532395
DATED : August 27, 2019
INVENTOR(S) : Ruth Hinrichs et al.

Page 1 of 1

It is certified that error appears in the above-identified patent and that said Letters Patent is hereby corrected as shown below:

On the Title Page

In item (57), under "ABSTRACT", Line 4, delete "a-hydroxy" and insert -- α-hydroxy --, therefor.

In the Claims

In Column 13, Line 27, in Claim 6, after "claim 1", insert -- , --.

In Column 13, Line 37, in Claim 9, after "weight", insert -- % --.

In Column 14, Line 10, in Claim 15, after "α-hydroxy", insert -- acid --.

Signed and Sealed this
Eighteenth Day of February, 2020

Andrei Iancu
*Director of the United States Patent and Trademark Office*